United States Patent [19]

Schmidt-Rabenau et al.

[11] 4,285,791
[45] Aug. 25, 1981

[54] ELECTRODE SYSTEM

[75] Inventors: Hartmut Schmidt-Rabenau, Hamburg; Hans-Werner Berger, Jersbek, both of Fed. Rep. of Germany

[73] Assignee: Eppendorf Geratebau Netherler + Hinz GmbH, Hamburg, Fed. Rep. of Germany

[21] Appl. No.: 165,728

[22] Filed: Jul. 3, 1980

[30] Foreign Application Priority Data

Jul. 6, 1979 [DE] Fed. Rep. of Germany ....... 2927361

[51] Int. Cl.³ ............................................ G01N 27/30
[52] U.S. Cl. ................................................ 204/195 M
[58] Field of Search ..................... 204/195 M; 128/635

[56] References Cited
U.S. PATENT DOCUMENTS

| 3,442,782 | 5/1969 | Shiller et al. | 204/195 M |
| 3,591,480 | 7/1971 | Neff et al. | 204/195 M |
| 4,216,068 | 8/1980 | Schindler et al. | 204/195 R |

Primary Examiner—G. L. Kaplan
Attorney, Agent, or Firm—Richard D. Weber

[57] ABSTRACT

An electrode assembly for electro-chemical measuring systems includes an electrode member having a selectively sensitive membrane disposed in its front end and an electrical conductor extending from the membrane rearwardly through the electrode member. A holding member is provided to secure the electrode member in sealed relation with the membrane disposed within a measuring chamber. The holding member provides a spring loaded sealing force to the electrode member and can be applied and removed without rotation of the electrode member.

5 Claims, 3 Drawing Figures

ELECTRODE SYSTEM

BACKGROUND OF THE INVENTION

The present invention relates generally to electrochemical measuring systems and relates more particularly to an electrode assembly for such a system. The present electrode assembly includes an electrode member adapted for introduction into the bore of a measuring chamber and having a selectively sensitive membrane disposed in its front end and an electrical conductor extending from the membrane rearwardly through the electrode member. A holding member which is engageable with the element defining the measuring chamber bore is provided for securing the electrode member in position within the bore.

In a known system of this type (German Offenlegungsschrift No. 2,212,801) the electrode member which carries the selectively sensitive membrane is inserted in a bore on the lower end of which are located supply and discharge channels for the sample to be analysed, so that said samples can be brought into contact with the membrane. A cup-shaped holding member is threadedly attached to the rear end of the bore wall extended in a tubular manner for securing the electrode member in the bore and for sealing purposes. In addition, an O-ring is placed between the holding member and the electrode member to provide a seal. The conductive connection is passed out of the electrode member through the base wall of the holding member.

With such a system due to the rotary movement required to attach the threaded holding member, there is a corresponding rotary movement of the electrode member about its longitudinal axis with the danger that the very sensitive membrane may engage the peripheral areas of the supply and discharge channels at the front end of the electrode member resulting in damage thereto. Furthermore, the holding force acting in the longitudinal direction on the electrode member can only be accurately adjusted with considerable difficulty due to the threaded attachment of the holding member, so that there is either a risk of leaks or of the electrode member being damaged.

It is also known (German Offenlegungsschrift No. 2,726,772) to construct the electrode member from a plastic member carrying the membrane and which is firmly connected with a rear metal mounting having an external thread for screwing into the bore wall, as well as a contact to which the electrical conductor is connected.

Quite apart from the fact that this known arrangement is complicated and costly to manufacture, the difficulty once again arises that a rotary movement is necessary for mounting the electrode member which can damage the membrane while the force acting in the axial direction of the secured electrode member can only be gauged with great difficulty, so that the electrode member is frequently either secured too firmly or too loosely in the bore wall, which can impair the sealing effect. Finally, in these known electrode systems where polytetrafluoroethylene (PTFE) is used as the plastics material for the electrode member, under the action of mechanical pressure the plastic exhibits flow phenomena, so that after a certain time there is a deterioration in the seal between the front end face of the electrode member and the measuring chamber, making it necessary to subsequently regularly adjust the screw connection.

SUMMARY OF THE INVENTION

The object of the invention is to provide an electrode assembly in which the electrode member is placed in the measuring chamber in such a way that damage to the electrode membrane is reliably avoided and where a completely satisfactory, durable sealing of the measuring chamber is obtained.

According to the invention, this problem is solved by an electrode assembly of the type described hereinbefore in which the holding member has an inner body which engages the electrode member and which, with respect to the connecting portion of the holding member engageable with the element defining the bore wall, can be moved to a limited extent in the axial direction against spring pressure and can be rotated about the longitudinal axis of the holding member.

Thus, in the electrode system according to the invention, the part of the holding member which comes into contact with the electrode member is axially and rotationally movable with respect to the connecting portion of the holding member and, on forming the connection between the holding member and the bore wall, preferably by means of a bayonet connection, although the connecting member is given a certain rotary movement, the inner body of the holding member and the electrode member remain substantially in a non-rotated position, so that there is no risk of damage to the membrane.

Furthermore, due to the spring pressure acting on the inner body, a constant predetermined force is axially exerted on the electrode member and the adjustment difficulties for this force encountered with the known electrode systems are reliably avoided.

In particular, if the electrode member is made from a plastics material, such as polytetrafluoroethylene which flows under pressure action, it is possible to obtain a reliable and invariable seal between the electrode member and the measuring chamber by placing a ring seal over the front end face of the electrode member which projects beyond said face and surrounds the membrane. This ring seal, which essentially has the shape of an O-ring and is fitted in a slot in the front end face of the electrode member, forms the sealing engagement between the measuring chamber wall and the front end face of the electrode member, so that the plastics material of the electrode member is not loaded to such an extent in said area that flow phenomena need be feared and damage to the membrane is prevented.

In order when mounting the electrode member in the bore to provide an outwardly leading connection with the electrical conductor of the electrode member, the inner body includes a connecting element which is accessible from the outside and can be brought into contact with the conductor. At its rear end, the inner body can also have a terminal connected with the connecting element and to which the associated circuit can be very easily connected.

The invention is described in greater detail hereinafter with respect to a preferred embodiment as illustrated in the attached drawings.

DESCRIPTION OF THE PREFERRED EMBODIMENT

Figure 1:
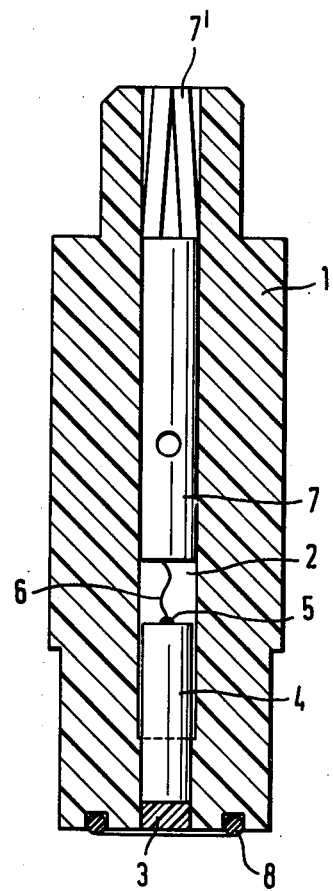
FIG. 1 is a longitudinal sectional view through an electrode member.

An electrode assembly in accordance with the present invention includes an electrode member 1 as shown in FIG. 1 and which is for example made from a plastics material such as polytetrafluoroethylene. The electrode member 1 has an axially extending central bore 2 into the front end of which is inserted an electrically conductive element 4, such as of platinum or silver which carries a diagrammatically indicated membrane 3 on its front face. From a connection 5 on the rear end of element 4, a conductive wire 6 leads to a conductive bushing 7 inserted in central bore 2 and which includes a slotted rear terminal portion 7' adapted to receive a rod-shaped element therein.

The front end of electrode member 1 has an annular slot in which is inserted an elastic ring seal 8 which is disposed concentrically with respect to the membrane 3 and extends beyond the front end face of electrode member 1.

Figure 2:
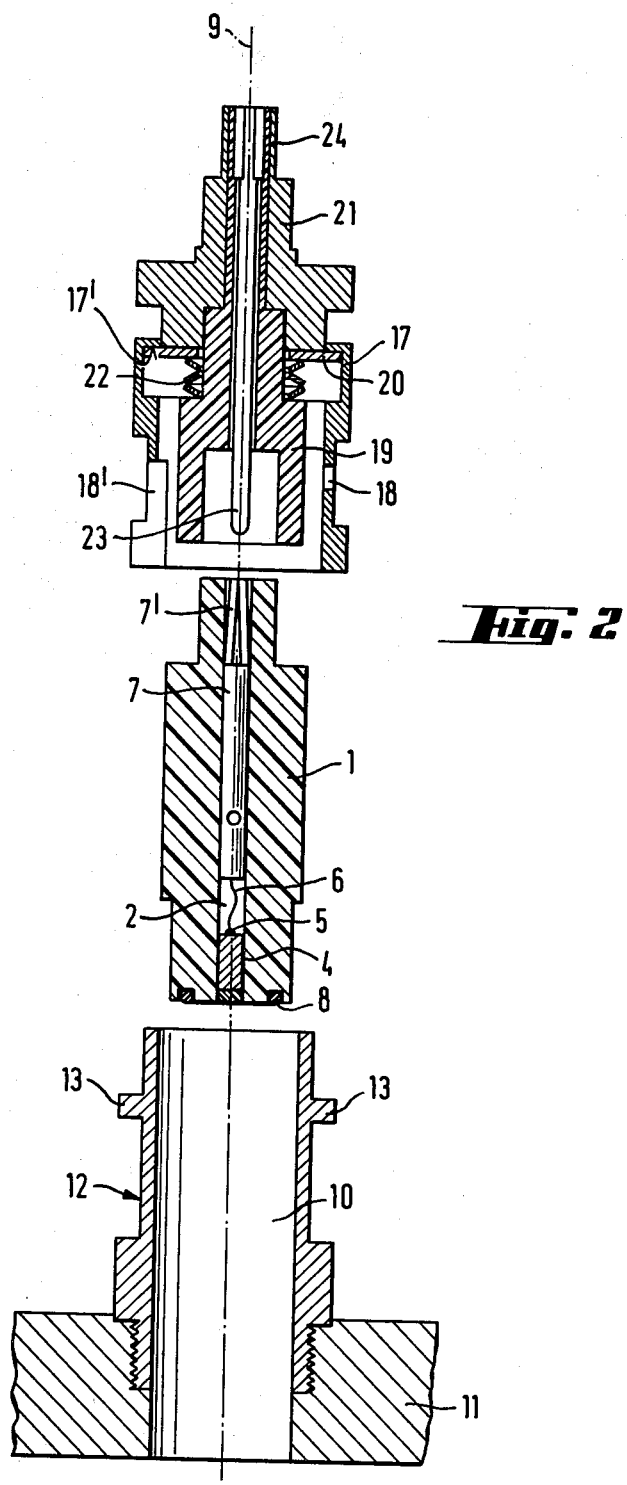
FIG. 2 is an exploded longitudinal sectional view of the tubular member, the electrode member and the holding member.
Figure 3:
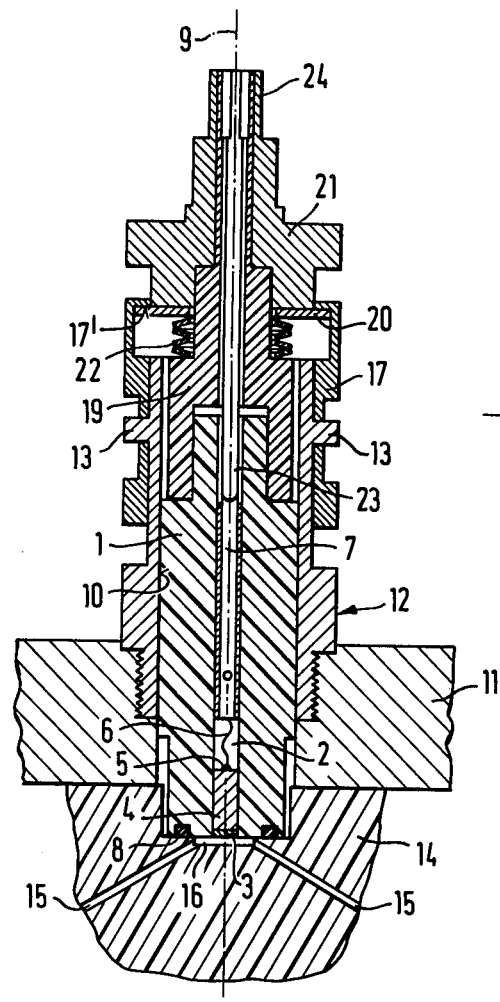
FIG. 3 is a longitudinal sectional view of the electrode assembly according to FIG. 2 in the assembled state.

The manner in which electrode member 1 is positioned and secured in the electrode assembly can be gathered from FIGS. 2 and 3 and the following description.

As shown, supply and discharge channels 15 for samples to be analysed are provided in a measuring chamber member 14 (FIG. 3) and they terminate in a measuring chamber 16 into which extends the membrane 3. The measuring chamber member 14, which may be made of a plastic material, is disposed against a wall 11, e.g. of stainless steel, through which runs the bore 10 which opens into the measuring chamber member 14. The bore 10 extends beyond the wall 11 through a tubular metal member 12 fixed in casing wall 11 which serves as a receiver for the electrode member 1. The electrode member 1 is placed in the tubular member 12, so that the membrane 3 is located in the measuring chamber 16 and the ring seal 8 engages the juxtaposed wall of the measuring chamber 16 (FIG. 3).

The holding member comprising a connecting member 17 and a two-part inner body 19, 21 serves to sealingly secure the electrode member. Spaced from its front end, the wall of connecting member 17 has recesses 18 which are connected to circumferentially displaced slots 18' (only one is shown) extending from the front end of connecting member 17. Corresponding to the dimensions of recesses 18, projections 13 are provided on the outer wall of tubular member 12, which extend rearwardly along the slots 18' in the wall of connecting member 17 and which by a rotary movement of the connecting member can be engaged with the recesses 18, so that a bayonet connection is formed, as shown in FIG. 3.

On forming this bayonet connection, the front edge of the inner body portion 19, which consists of an electrically insulating material, engages a shoulder of electrode member 1 and is moved rearwards against the pressure of spring 22 which is supported on a disk 20 engaging an inwardly facing flange 17' of connecting member 17. As a result, the inner body portion 21 connected to inner body 19 is correspondingly displaced rearwards with respect to connecting member 17. Accordingly, upon completing the bayonet connection of the holding member to secure the electrode member 1, the force which presses the ring seal against the juxtaposed surface of measuring chamber member 14 is substantially determined by the compression of spring 22.

With respect to the connecting member 17, inner body portions 19 and 21 are rotatable about the longitudinal axis 9 of the connecting member and the electrode member 1, so that during rotation of the connecting member 17 to form the bayonet connection, the inner body 19, 21 does not rotate. Since the connecting member 17 is not in contact with the electrode member 1 and since the latter is merely pushed downwards into the bore by the inner member portion 19, electrode member 1 is not subject to rotary movement prejudicial to membrane 3.

The inner body contains a rod-shaped, electrically conductive connecting element 23 disposed coaxially with the longitudinal axis of the holding member and therefore coaxially with the central bore 2 of electrode member 1 in the assembled state. The front end of this connecting element 23 is inserted during assembly (cf FIG. 3) into the slotted rear terminal portion 7' of conductive bushing 7 and is brought into electrically conductive contact with the latter, so that by means of connecting element 23 an electrical connection with membrane 3 is produced which is accessible from outside the electrode assembly. The rear end 24 of inner body portion 21 consists of metal and is constructed as a contact to which a connection may be made to the corresponding circuit.

We claim:

1. An electrode system comprising means defining a bore of a measuring chamber, an electrode member which can be introduced into said bore with a selectively sensitive membrane disposed in its front end and an electrical conductor extending from said membrane rearwardly through the electrode member, a holding member which can be engaged with said bore defining means for securing said electrode member upon insertion in said bore, characterized in that said holding member comprises an inner body which engages said electrode member, and a connecting portion which engages said bore defining means and wherein said connecting portion can be moved to a limited extent in the axial direction of said holding member and electrode member against spring pressure and can be rotated about the longitudinal axis of the holding member.

2. An electrode system according to claim 1, characterized in that said holding member inner body has a connecting element which is accessible from the outside and can be brought into contact with said electrical conductor.

3. An electrode system according to claim 2, characterized in that a contact is provided on the rear end of said inner body which is electrically connected with said connecting element.

4. An electrode system according to claim 1, comprising bayonet connector means for detachably connecting said holding member and said bore defining means.

5. An electrode system according to claim 1, characterized in that a ring seal is provided in the front end face of said electrode member which projects beyond said end face and surrounds said membrane.

* * * * *